United States Patent [19]

Stemp

[11] 4,427,685
[45] Jan. 24, 1984

[54] CYCLOALKYLAMINO DERIVATIVES AND THEIR USE IN THE TREATMENT OF PEPTIC ULCERS AND THE LIKE

[75] Inventor: Geoffrey Stemp, Sawbridgeworth, England

[73] Assignee: Beecham Group P.L.C., England

[21] Appl. No.: 345,424

[22] Filed: Feb. 3, 1982

[30] Foreign Application Priority Data

Feb. 9, 1981 [GB] United Kingdom ............... 8103844
Nov. 21, 1981 [GB] United Kingdom ............... 8135162

[51] Int. Cl.³ .................... A61K 31/13; A61K 31/34; A61K 31/38; C07D 307/52
[52] U.S. Cl. ........................ 424/267; 549/76; 546/230; 546/231; 549/479; 548/517; 548/527; 549/492; 548/567; 548/569; 549/493; 549/494; 549/495; 549/496; 549/60; 549/65; 549/74; 549/75; 564/27; 564/47; 564/89; 564/91; 564/92; 564/104; 564/108; 564/237; 564/306; 424/274; 424/275; 424/285; 424/304; 424/321; 424/322; 424/324; 424/326; 424/330; 542/416; 546/213; 546/214
[58] Field of Search ............... 549/60, 65, 74, 75, 549/76, 479, 492, 493, 494, 495, 496; 548/517, 527, 567, 569; 546/213, 214, 230, 231; 542/416; 564/27, 47, 89, 91, 92, 104, 108, 237, 306; 424/267, 274, 275, 285, 304, 321, 322, 324, 326, 330

[56] References Cited

U.S. PATENT DOCUMENTS 4,128,658 12/1978 Price et al. ............... 549/491 X
4,203,909 5/1980 Algieri et al. ............ 549/495
4,233,302 11/1980 Martin-Smith et al. ..... 549/479 X

FOREIGN PATENT DOCUMENTS 6008380 1/1981 Australia .
2821410 5/1978 Fed. Rep. of Germany .

Primary Examiner—Richard Raymond
Attorney, Agent, or Firm—Jacobs & Jacobs

[57] ABSTRACT

Compounds of formula (I) and pharmaceutically acceptable salts thereof:

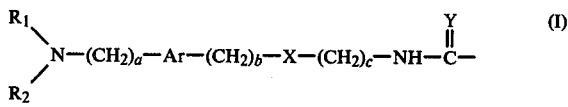

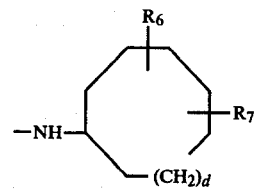

wherein:
a is 1 to 3;
b is 0 to 2;
c is 2 to 4;
d is 1 to 5;
X is sulphur, oxygen or —$CH_2$—;
Y is oxygen, sulphur, $NR_4$ or $CHR_5$ wherein $R_4$ is hydrogen, $C_{1-4}$ alkyl, $NO_2$ or CN, $C_{1-4}$ alkylsulphonyl or phenylsulphonyl optionally substituted in the phenyl moiety by one or two substituents selected from $C_{1-4}$ alkyl, $C_{1-4}$ alkoxy, fluorine, chlorine or bromine, and $R_5$ is $NO_2$, $C_{1-4}$ alkylsulphonyl or optionally substituted phenylsulphonyl as defined for $R_4$;
$R_1$ and $R_2$ are independently hydrogen, $C_{1-4}$ alkyl, or $C_{3-6}$ cycloalkyl; or $R_1$ and $R_2$ taken together with the nitrogen to which they are attached represent a pyrrolidino or piperidino ring;
$R_6$ and $R_7$ are independently hydrogen or $C_{1-6}$ alkyl; and
Ar is furan or thiophene attached at positions 2- and 5- or benzene attached at positions 1- and 3- or 1- and 4-, having useful pharmacological activity, processes for their preparation and their use.

9 Claims, No Drawings

CYCLOALKYLAMINO DERIVATIVES AND THEIR USE IN THE TREATMENT OF PEPTIC ULCERS AND THE LIKE

This invention relates to novel compounds, to pharmaceutical compositions containing them, and to a process for their preparation.

U.S. Pat. No. 4,128,658 discloses that compounds of the formula (A):

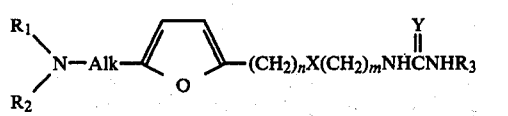

and physiologically acceptable salts and N-oxides and hydrates thereof, in which $R_1$ and $R_2$ which may be the same or different represent hydrogen, lower alkyl, cycloalkyl, lower alkenyl, aralkyl or lower alkyl interrupted by an oxygen atom or a group

in which $R_4$ represents hydrogen or lower alkyl or $R_1$ and $R_2$ may, together with the nitrogen atom to which they are attached, form a heterocyclic ring which may contain other (optionally substituted) heteroatoms selected from O and

$R_3$ is hydrogen, lower alkyl, lower alkenyl or alkoxyalkyl;

X is —$CH_2$—, O or S;

Y represents =S, =O, =$NR_5$ or =$CHR_6$;

Alk denotes a straight or branched alkylene chain of 1 to 6 carbon atoms;

$R_5$ is H, nitro, cyano, lower alkyl, aryl, alkylsulphonyl, or arylsulphonyl;

$R_6$ represents nitro, arylsulphonyl or alkylsulphonyl;

m is an integer from 2 to 4; and n is 1 or 2; or when X=S, or —$CH_2$—, n is zero, 1 or 2; are histamine $H_2$-receptor antagonists, and thus may be used in the treatment of disorders related to excess gastric acid secretion such as peptic ulcer.

European Patent Application No 79300754.3 (Publication No 0006679) discloses a class of thiadiazole derivatives having a side chain terminating in a vast number of different moieties, including —N—$C_{3-6}$ cycloalkyl.

A class of compounds has now been discovered which is structurally distinct from the compounds of the said U.S. Patent and European Patent Application and which also has useful histamine $H_2$-receptor antagonist activity. The present class of compounds also has cholinergic activity.

Accordingly, the present invention provides a compound of formula (I), and pharmaceutically acceptable salts thereof:

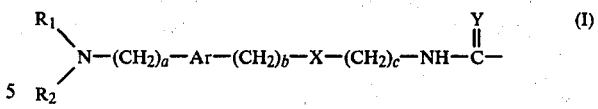

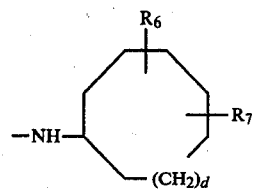

wherein:
a is 1 to 3;
b is 0 to 2;
c is 2 to 4;
d is 1 to 5;
X is sulphur, oxygen or —$CH_2$—;
Y is oxygen, sulphur, $NR_4$ or $CHR_5$ wherein $R_4$ is hydrogen, $C_{1-4}$ alkyl, $NO_2$ or CN, $C_{1-4}$ alkylsulphonyl or phenylsulphonyl optionally substituted in the phenyl moiety by one or two substituents selected from $C_{1-4}$ alkyl, $C_{1-4}$ alkoxy, fluorine, chlorine or bromine, and $R_5$ is $NO_2$, $C_{1-4}$ alkylsulphonyl or optionally substituted phenylsulphonyl as defined for $R_4$;

$R_1$ and $R_2$ are independently hydrogen, $C_{1-4}$ alkyl, or $C_{3-6}$ cycloalkyl; or $R_1$ and $R_2$ taken together with the nitrogen to which they are attached represent a pyrrolidino or piperidino ring;

$R_6$ and $R_7$ are independently hydrogen or $C_{1-6}$ alkyl; and

Ar is furan or thiophene attached at positions 2- and 5- or benzene attached at positions 1- and 3- or 1- and 4-.

Suitable examples of a include 1 and 2, preferably 1.

Suitable examples of b include 0 and 1.

Suitable examples of c include 2 and 3, preferably 2.

d may suitably be any of the integers 1 to 5. Often d will be 1 or 2, such as 1.

Often X will be S.

In Y, suitable examples of $R_4$ include hydrogen, methyl, ethyl, and CN, and of $R_4$ and $R_5$ include $NO_2$, methylsulphonyl, ethylsulphonyl, n- and iso-propylsulphonyl and n-, iso- and tert butylsulphonyl, and phenylsulphonyl optionally substituted in the phenyl moiety by one or two substituents selected from $C_{1-4}$ alkyl, (such as methyl), $C_{1-4}$ alkoxy (such as methoxy), fluorine, chlorine or bromine.

More suitably, Y is O, S, NH, $NCH_3$, $NNO_2$, NCN or $CHNO_2$. Preferably Y is S, NCN or $CHNO_2$.

Examples of suitable $R_1$ and $R_2$ groups include hydrogen; methyl and ethyl; cyclopropyl and cyclohexyl; and of $R_1R_2N$; pyrrolidino. When one of $R_1$ and $R_2$ is cycloalkyl, often the other of $R_1$ and $R_2$ will be hydrogen.

Often $R_1$ and $R_2$ will both be alkyl, for example dimethyl.

Suitable examples of $R_6$ and $R_7$ include hydrogen, methyl, ethyl, n- and iso-propyl, n, sec and tert-butyl. Often $R_3$ and $R_4$ are both hydrogen.

Suitable examples of Ar include furan, thiophene or benzene attached at positions 1- and 3-. Favourably, Ar is furan.

Suitable examples of the salts of the compounds of the formula (I) include those derived from hydrochloric hydrobromic, phosphoric, sulphuric, acetic, citric, tartaric or maleic acids.

There is a group of compounds within formula (I) wherein b is 1, d is 1 to 4, X is sulphur or —CH$_2$—, R$_6$ and R$_7$ are both hydrogen, Ar is furan attached at positions 2- and 5- and the remaining variables are as defined in formula (I).

From the aforesaid it will be appreciated that one useful sub-group of compounds is of formula (II):

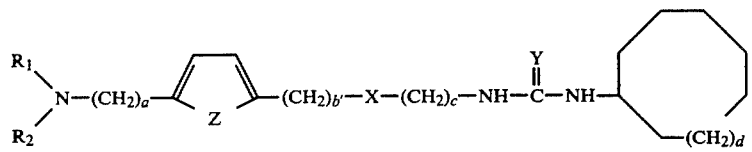

wherein
Z is oxygen or sulphur;
b′ is 1 or 2 and the other variables are as defined in formula (I).

Suitable and preferred examples of the variables in formula (II) are as described for the corresponding variables in formula (I).

A favourable sub-group of compounds within formula (II) is of formula (III):

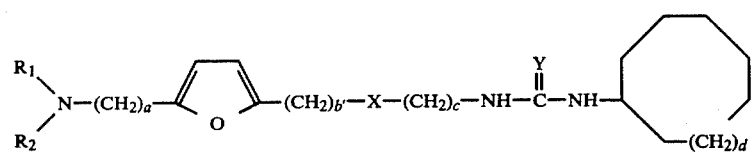

wherein the variables are as defined in formula (I) and formula (II).

Suitable and preferred examples of the variables in formula (III) are as described for the corresponding variables in formula (I).

Suitable examples of a include 1 or 2, preferably 1.
b′ is aptly 1.
Often c will be 2 or 3.
Aptly in formula (III) X may be S.
In formula (III) Y may suitably be S, NCN or CHNO$_2$, for example CHNO$_2$.

Also in formula (III) R$_1$ and R$_2$ will often be, independently, hydrogen or C$_{1-4}$ alkyl, such as for example dimethyl.

A further sub-group of interest is of formula (IV):

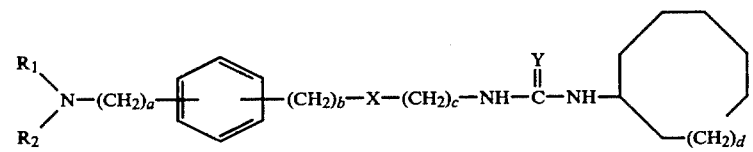

wherein the variables are as defined in formula (I).
Favourably b is 0 and c is 3.
Often X is oxygen.

The compounds of the formula (I) are histamine H-2 receptor antagonists, and accordingly have gastric acid secretion inhibitory activity and possible anti-inflammatory activity. Thus the compounds may be used in the treatment or prophylaxis of any disorder caused or exacerbated by excess gastric acid secretion, such as in particular peptic ulcers or in the treatment of inflammation.

The compounds also have cholinergic activity, which in combination with histamine H-2 receptor antagonist activity could make them particularly useful in the treatment of reflux oesophagitis.

Accordingly, the invention also provides a pharmaceutical composition comprising the compound of formula (I), or a pharmaceutically acceptable salt thereof, and a pharmaceutically acceptable carrier.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For the parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration.

The compound can be sterilized by exposure to ethylene oxide before suspending in the sterile vehicle. Advantageously, a surfactant or wetting agent is included in the composition to facilitate uniform distribution or the compound.

When appropriate the compositions of this invention may be presented as an aerosol for oral administration, or as a microfine powder for insufflation.

As is common practice, the compositions will usually be accompanied by written or printed directions for use in the medical treatment concerned.

By way of example, unit dose compositions will suitably contain from 10 to 2 000 mg, more preferably from 50 to 1 000 mg of the active ingredient.

It will be appreciated of course that the quantity of the compound administered to the sufferer each day will depend on the usual factors such as the severity of the disease and the weight of the sufferer. Suitably however it is believed that between 1 to 30 mg/kg/day of the compound will be administered to achieve satisfactory therapy. Such administration is conveniently effected with repeated dosing throughout the day of the composition in unit dose form.

The invention also provides a method of treatment and/or prophylaxis of disorders carried or exacerbated by excess gastric acid secretion, such as peptic ulcers, in mammals including humans, which comprises the administration of an effective amount of the compound of the invention.

The invention also provides a process for the preparation of a compund of the formula (I), which process comprises reacting a compound of formula (V):

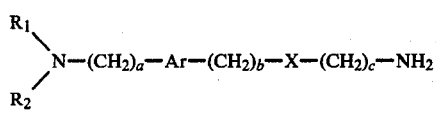

with a compound capable of introducing the group of formula (VI):

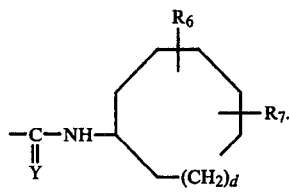

The amine of formula (V) may be used in this reaction as the free base, or in the form of a salt with an acid, for example acetic acid.

Compounds which are capable of introducing the group of formula (VI) include isocyanates, isothiocyanates and compounds of the formula (VII) and (VIII):

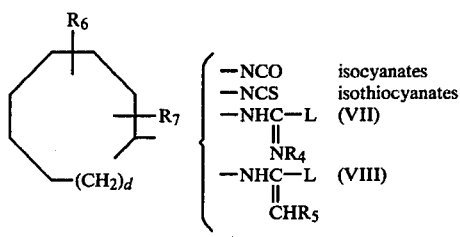

wherein L is a leaving group readily displaceable by a nucleophile.

The reaction with an isocyanate or isothiocyanate may be carried out by allowing the reactants to stand in a solvent, such as acetonitrile.

The reaction with a compound of formula (VII) or a compound of formula (VIII) may be carried out by heating the reactants at an elevated temperature, for example 60°–140° C., optionally in a solvent such as water, ethanol or dichloroethane.

Suitable examples of the leaving group L include halogen, thiomethyl or lower alkoxy, preferably thiomethyl.

The invention also provides a further process for the preparation of compounds of the formula (I) wherein Y is NR$_4$ or CHR$_5$, which process comprises reacting a compound of formula (IX):

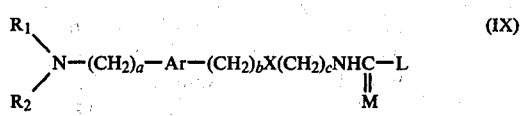

wherein M is NR$_4$ or CHR$_5$, with an amine

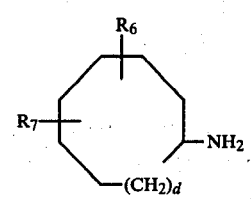

This reaction is suitably carried out at a temperature from ambient to reflux.

The compound of formula (IX) may itself be prepared from a compound of formula (V) by reaction with a compound of formula (X):

This reaction may be effected in a solvent, for example ethanol or acetonitrile or dichloroethane, at a temperature from ambient to reflux.

Compounds of formula (V) are either known compounds, or may be prepared in analogous method to known compounds.

The following Examples illustrate the preparation of compounds of the invention.

The following Pharmacological Data Section illustrates the useful activity of the compounds of the invention.

EXAMPLE 1

N-[2-[[[5-(Dimethylamino)methyl-2-furanyl]methyl]thio]ethyl]-N'-cyclooctyl-2-nitro-1,1-ethenediamine

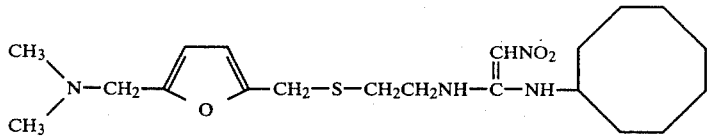

A solution of 1,1-bismethylthio-2-nitroethene (2.9 g, 17.6 mmol) and 2-[[[5-dimethylamino)methyl-2-furanyl]methyl]thio]ethanamine (3.7 g, 17.6 mmol) in 1,2-dichloroethane (30 ml) was heated at 70°–75° C. for 6 hours. The solvent was then removed by distillation under reduced pressure, and the residue was chromatographed on a column of silica (ethyl acetate:methanol, 4:1) to give 1-(methylthio)-1-[2[[[5-dimethylamino)-methyl-2-furanyl]methyl]thio]ethylamino]-2-nitroethane (2.2 g, 40%), as an oil. [NMR τ (CDCl₃), —0.60 br (s, 1H), 3.50 (s, 1H), 3.90 (s, 2H), 6.20 (s, 2H), 6.30–6.60 (m, 4H), 7.10–7.40 (m, 2H), 7.50 (s, 3H), 7.80 (s, 6H)].

A solution of 1-(methylthio)-1-[2-[[[5-(dimethylamino) methyl-2-furanyl]methyl]thio]ethylamino]2-nitroethene (1.05 g, 3.2 mmol) and cyclooctyl amine (1.2 g, 9.5 mmol) in ethanol (20 ml) was stirred at 20° C. for 21 days. The solvent was then removed in vacuo and the residue was chromatographed on a column of alumina (using chloroform as eluant) to give N-[2-[[[5-dimethylamino)-methyl-2-furanyl]methyl]thio]ethyl]-N'-cyclooctyl-2-nitro-1,1-ethenediamine (0.51 g, 39%) as an oil. [NMR τ (CDCl₃) —0.30 br (s, 1H), 3.46 (s, 1H), 3.85 (s, 2H), 6.20 (s, 2H), 6.56 (s, 2H), 6.30–6.90 (m, 3H), 7.15–7.30 (m, 2H), 7.75 (s, 6H), 8.00–8.70 (m, 14H)]. [Found [M+H]+ 411.2391; C₂₀H₃₅N₄O₃S requires [M+H]+ 411.2429.]

Similarly prepared were Examples 2 and 3.

EXAMPLE 2

N-[2-[[[5-(Dimethylamino)methyl-2-furanyl]methyl]thio]ethyl]-N'-cyclononyl]-2-nitro-1,1-ethenediamine

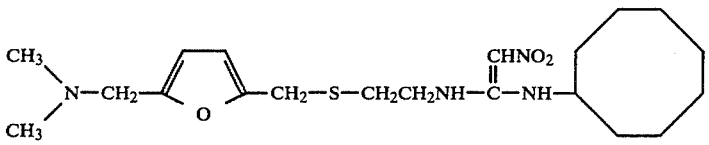

τ (CDCl₃): —0.4 br s (1H), 3.50 (s, 1H), 3.85 (m, 2H), 6.25 (s, 2H), 6.40 (m, 1H), 6.55 (s, 2H), 6.75 (m, 2H), 7.25 (t, 2H), 7.75 (s, 6H), 8.10–8.60 (m, 16H). [Found: MH+ 425; C₂₁H₃₆N₄O₃S requires MH+ 425].

EXAMPLE 3

N-[2-[[[5-(Dimethylamino)methyl-2-furanyl]methyl]thioethyl]-N'-cyclododecyl]-2-nitro-1,1-ethenediamine

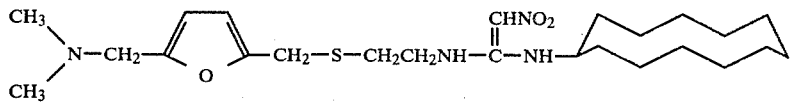

τ(CDCl₃): 3.23 (s, 1H), 3.85 (m, 2H), 4.75 br(s, 2H), 6.27 (s, 2H), 6.45 (m, 1H), 6.65 (s, 2H), 6.75 (m, 2H), 7.25 (t, 2H), 7.75 (s, 6H), 8.25–8.80 (m, 22H). [Found: MH+ 467.3072; C₂₄H₄₂N₄O₃S requires MH+ 467.3091].

EXAMPLE 4

N-[2-[[5-(Dimethylamino)methyl-2-thienyl]methyl]thioethyl]-N-cyclooctyl-2-nitro-1,1-ethenediamine

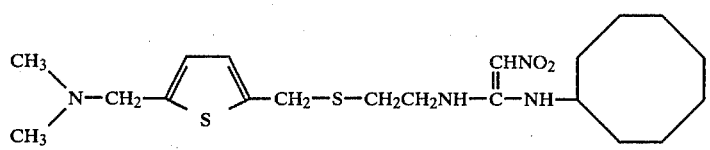

A solution of 2-[[[5-(dimethylamino)methyl-2-thienyl]methyl]thio]ethanamine (1.00 g) and 1-cyclooctylamino-1-methylthio-2-nitroethene (1.17 g) in acetonitrile (4 ml) was heated at reflux temperature for 8 days. The solvent was then evaporated in vacuo and the residue partitioned between water (25 ml) and ethyl acetate (25 ml). The aqueous phase was then extracted with ethyl acetate (2×25 ml) and the combined organic extracts were dried (Na₂SO₄) and evaporated in vacuo. The residue was purified by column chromatography on alumina using pentane/chloroform mixtures as eluant to give N-[2-[[5-(dimethylamino)methyl-2-thienyl]-methyl]thioethyl]-N-cyclooctyl-2-nitro-1,1-ethenediamine (0.62 g) as an orange oil.

[NMR τ(CDCl₃) —0.35 br (s, 1H), 3.3 (m, 2H), 3.5 (s, 1H), 6.1 (s, 2H), 6.41 (s, 2H), 6.3–6.9 br (m, 3H), 7.25 (t, 2H), 7.7 (s, 6H), 7.9–8.6 br (M, 14H)].

C₂₀H₃₄N₄O₂S₂: Found [M+H]+ 427.2192, Requires [M+H]+ 427.2201.

EXAMPLE 5

N-[3-[3-[(dimethylamino)methyl]phenoxy]propyl]-2-nitro-1,1-ethenediamine

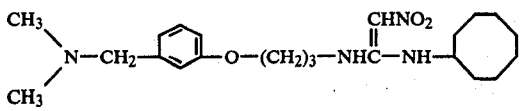

A solution of 3-[3-[(dimethylamino)methyl]phenoxy]propylamine (0.28 g) and 1-cyclooctylamino-1-methylthio-2-nitroethene (0.36 g) in acetonitrile (5 ml) was heated at 80° for 10 days. The solvent was then evaporated in vacuo and the residue partitioned between water (15 ml) and chloroform (15 ml). The aqueous phase was then extracted with chloroform (2×25 ml) and the combined organic extracts were washed with brine (50 ml), dried ($Na_2SO_4$) and evaporated in vacuo. The residue was purified by column chromatography on alumina using pentane/chloroform mixtures as eluant to give N-[3-[3-[(dimethylamino)methyl]phenoxy]propyl]-2-nitro-1,1-ethenediamine (0.14 g) as an orange oil.

[NMR $\tau$(CDCl$_3$) −0.5 br(s, 1H), 2.75-3.4 (m, 4H), 3.9 (s, 1H), 4.5 br (s, 1H), 5.9 (t, 2H), 6.6 (s, 2H), 6.2-6.8 (m, 3H), 7.8 (s, 6H), 7.85 (m, 2H), 8-8.75 br(m, 14H)].

$C_{22}H_{36}N_4O_3$: Found [M−H]+ 403.2737 Requires [M−H]+ 403.2709.

EXAMPLE 6

N-Cyclooctyl-N'-[3-[[3-(1-piperidinyl)methyl]phenoxy]propyl]-2-nitro-1,1-ethenediamine

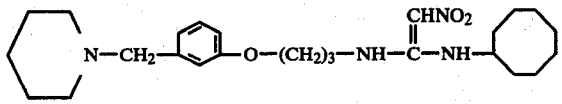

A solution of 1,1-bismethylthio-2-nitroethene (1.33 g, 8.1 mmole) and 3-[[3-(1-piperidinyl)methyl]phenoxy]propylamine (2.00 g, 8.1 mmol) in acetonitrile (20 ml) was heated at reflux temperature for 3 hours under nitrogen. The solvent was evaporated in vacuo to give 1-methylthio-1-[3-[[3-(1-piperidinyl)methyl]phenoxy]propylamino]-2-nitroethene (2.97 g) as a pale orange oil.

A solution of 1-methylthio-1-[3-[[3-(1-piperidinyl)methyl]phenoxy]propylamino]-2-nitroethene (2.94 g, 8.1 mmol) and cyclooctylamine (1.03 g, 8.1 mmol) in acetonitrile (25 ml) was heated at reflux temperature. After 24 hours further cyclooctylamine (0.5 g, 3.9 mmol) was added and the heating continued for a further 3 days. The solvent was then evaporated in vacuo and the residue was purified by column chromatography on a column of alumina (using n-pentane-chloroform mixtures as eluant) to give N-cyclooctyl-N'-[3-[[3-(1-piperidinyl)methyl]phenoxy]propyl]-2-nitro-1,1-ethenediamine (1.35 g) as an off white powder m.p. 119°-122°.

$C_{25}H_{40}N_4O_3$: Found C: 67.47, H: 9.19, N: 12.42%, Requires C: 67.54, H: 9.07, N: 12.60%.

EXAMPLE 7

N-Cyano-N'-cyclooctyl-N''-(2-[[[5-(dimethylamino)-methyl-2-furanyl]-methyl]thio]ethyl)-guanidine

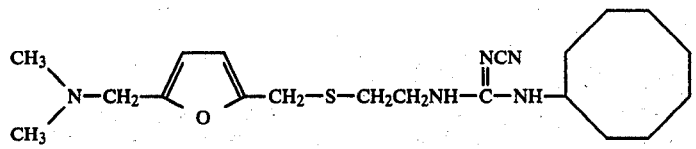

A solution of N-cyanoimidocarbamodithioic acid, dimethyl ester (7.0 g, 48 mmol) and cyclooctylamine (6.5 g, 51 mmol) in acetonitrile (100 ml) was heated under reflux for 4 hours. The solution was cooled in an ice bath and the solid which separated was filtered off to give N-cyano-N'-cyclooctylcarbaminidothioic acid, methyl ester as colourless plates (9.8 g) m.pt. 78°-80° C.

A solution of 2-[[[5-(dimethylamino)methyl-2-furanyl]methyl]thio]ethanamine (1.0 g, 4.7 mmol) and N-cyano-N'-cyclooctylcarbaminidothioic acid, methyl ester (0.10 g 4.4 mmol) in ethanol (50 ml) was heated under reflux for 7 days. The solvent was then removed in vacuo and the residue was chromatographed on a column of alumina (using chloroform as eluant) to give N-cyano-N'-cyclooctyl-N''-(2-[[[5-(dimethylamino)-methyl-2-furanyl]methyl]thio]ethyl)guanidine (0.61 g, 36%) as an oil. [NMR $\tau$(COCl$_3$) 3.75 (m, 2H), 4.40 br (s, 1H), 4.75 br (s, 1H), 6.25 (s, 2H), 6.55 (s, 2H), 6.30-6.80 (m, 3H), 7.20-7.45 (m, 2H), 7.75 (s, 6H), 8.00-8.60 (m, 14H)]. [Found M.+ 391.2401; $C_{20}H_{33}N_5OS$ requires M.+ 391.2405].

Pharmacological Data Section

The histamine H-2 receptor antagonist activity of the compounds of the invention was investigated as follows:

Guinea-pig isolated atria

This test is designed to specifically detect histamine $H_2$-receptor antagonists. Guinea-pigs of either sex, weighing between 250 and 500 g, were killed by cervical dislocation and exsanguination. The heart was removed and placed in cold McEwens solution (1). The atria were dissected free and mounted in a jacketed 5 ml capacity tissue bath containing McEwens solution maintained at 32° C. and gassed with a 95% oxygen, 5% carbon dioxide gas mixture. Atrial beating was detected by an auxotonic lever and from thence recorded on a Devices MX2 hot wire pen recorder. Atrial rate was derived from the amplified force signal using a Devices Instantaneous Ratemeter and recorded on the MX2 pen recorder. The addition of histamine to the tissue bath resulted in increases in both the rate and force of atrial beating. To avoid disruption of the tissue by repeated washing, responses to cumulative concentrations of histamine were obtained in the absence (control) and then presence of various concentrations of test compounds. The ability to antagonise histamine mediated positive chronotropic responses of this tissue is believed to be specific for $H_2$-receptor antagonists. Such activity was assessed by examining the ability of test compounds to shift to the right the plotted concentration/response curves to histamine. A less than 5-fold decrease in histamine potency was taken as inactive, 5-10 fold as slightly active and 10 fold or greater as active.

See Table I.

The ability of the compounds of the invention to modify the pH of gastric acid secretion was investigated as follows:

The perfused rat stomach preparation

The modified (2) perfused stomach preparation (3) of the urethane (25% solution) anaesthetised rat, maintained at 34° C., allows the continuous measurement of pH during basal and stimulated acid secretion.

The lumen of the stomach of male Wistar rats (approximately 200 g bodyweight) was perfused, via a cannula designed to reduce the dead space of the stomach, with 5% glucose solution (37° C.) at the rate of 3 ml/min. The perfusate was forced over the surface of the secretory mucosa only, the antrum being excluded. The effluent then passed over a microflow-type glass pH electrode via a collecting funnel situated in the non-glandular forestomach.

The secretagogue histamine was administered as a constant intravenous infusion to produce a steady rate of acid secretion. Test compounds were administered in solution as bolus intravenous injections and any effect on the pH of the perfusate noted. The perfusate pH was recorded on a potentiometric recorder and anti-secretory responses were measured in terms of the maximal reduction in hydrogen-ion concentration expressed as a percentage of the "control" concentration.

See Table II.

References (1) McEwen, L. M. (1956). J. Physiol. (London), 131, 678-689.

(2) Ghosh, M. N. and Schild, H. O. (1958). Br. J. Pharmacol., 13, 54-61.

(3) Parsons, M. E. (1970). Ph.D. Thesis, University of London.

Toxicity

No toxic effects were observed in these tests.

TABLE I

| Compound Number | Concentration | Activity (Decrease in Histamine Potency) |
|---|---|---|
| 1 | $1 \times 10^{-6}$ M | Active (223-fold) |
|   | $1 \times 10^{31.7}$ M | Active (19-fold) |
| 2 | $1 \times 10^{-5}$ M | Active (16 fold) |
| 5 | $1 \times 10^{-6}$ M | Active (13 fold) |
| 6 | $1 \times 10^{-6}$ M | Slightly Active (8-fold) |

TABLE II

| Compound Number | Dose/$\mu$mol kg$^{-1}$ | Inhibition |
|---|---|---|
| 1 | 1-2 | 75-90% |
| 2 | 1-2 | 29-44% |
| 5 | 0.25-1 | 29-60% |

I claim:

1. A compound of formula (I), and pharmaceutically acceptable salts thereof:

$$R_1 \diagdown N-(CH_2)_a-Ar-(CH_2)_b-X-(CH_2)_c-NH-\overset{Y}{\underset{\|}{C}}- \text{(I)}$$
$$R_2 \diagup$$

[cycloalkyl ring with $-NH-$, $R_6$, $R_7$, $(CH_2)_d$ substituents]

wherein:
- a is 1 to 3;
- b is 0 to 2;
- c is 2 to 4;
- d is 1 to 5;
- X is sulphur, oxygen or $-CH_2-$;
- Y is oxygen, sulphur, NR$_4$ or CHR$_5$ wherein R$_4$ is hydrogen, $C_{1-4}$ alkyl, NO$_2$ or CN, $C_{1-4}$ alkylsulphonyl or phenylsulphonyl optionally substituted in the phenyl moiety by one or two substituents selected from $C_{1-4}$ alkyl, $C_{1-4}$ alkoxy, fluorine, chlorine or bromine, and R$_5$ is NO$_2$, $C_{1-4}$ alkylsulphonyl or optionally substituted phenylsulphonyl as defined for R$_4$;
- R$_1$ and R$_2$ are independently hydrogen, $C_{1-4}$ alkyl, or $C_{3-6}$ cycloalkyl; or R$_1$ and R$_2$ taken together with the nitrogen to which they are attached represent a pyrrolidino or piperidino ring;
- R$_6$ and R$_7$ are independently hydrogen or $C_{1-6}$ alkyl; and
- Ar is furan or thiophene attached at positions 2- and 5- or benzene attached at positions 1- and 3- or 1- and 4-.

2. A compound according to claim 1 of formula (III):

$$R_1 \diagdown N-(CH_2)_a-\langle\text{furan}\rangle-(CH_2)_{b'}-X-(CH_2)_c-NH-\overset{Y}{\underset{\|}{C}}-NH-\langle\text{cycloalkyl}(CH_2)_d\rangle \quad \text{(III)}$$
$$R_2 \diagup$$

wherein b' is 1 or 2 and the remaining variables are as defined in claim 1.

3. A compound according to claim 1, characterised in that a is 1 or 2, b respectively is 1, c is 2 and d is 1 or 2.

4. A compund according to claim 1, characterised in that X is sulphur.

5. A compound according to claim 1, characterised in that R$_1$ and R$_2$ are both methyl.

6. A compound according to claim 1, characterised in that Y is CHNO$_2$.

7. N-[2-[[[5-(Dimethylamino)methyl-2-furanyl]methyl]thio]ethyl]-N'-cyclooctyl-2-nitro-1,1-ethenediamine.

8. A pharmaceutical composition for the treatment of disorders caused or exacerbated by excess gastric acid secretion, which comprises an effective amount of a compound according to claim 1 or a pharmaceutically acceptable salt thereof, and a pharmaceutically acceptable carrier.

9. A method of treating disorders caused or exacerbated by excess gastric acid secretion in mammals, including humans, which method comprises administering an effective amount of a compound according to claim 1 or a pharmaceutically acceptable salt thereof to the sufferer.

* * * * *